United States Patent
Lei et al.

(10) Patent No.: US 8,376,968 B2
(45) Date of Patent: Feb. 19, 2013

(54) METHOD AND SYSTEM FOR QUANTIFYING AN INTENTION OF MOVEMENT OF A USER

(75) Inventors: Kin Fong Lei, Hong Kong (HK); Wallace Woon-Fong Leung, Hong Kong (HK)

(73) Assignee: The Hong Kong Polytechnic University, Kowloon (HK)

( * ) Notice: Subject to any disclaimer, the term of this patent is extended or adjusted under 35 U.S.C. 154(b) by 116 days.

(21) Appl. No.: 12/466,591

(22) Filed: May 15, 2009

(65) Prior Publication Data

US 2010/0292617 A1    Nov. 18, 2010

(51) Int. Cl.
*A61B 5/00* (2006.01)
(52) U.S. Cl. .................................................. 600/595
(58) Field of Classification Search ............. 600/546, 600/587, 595; 601/5
See application file for complete search history.

(56) References Cited

U.S. PATENT DOCUMENTS

| | | | |
|---|---|---|---|
| 7,236,832 B2 | 6/2007 | Hemmerling et al. | |
| 7,857,774 B2* | 12/2010 | Sankai | 601/5 |
| 2003/0068605 A1* | 4/2003 | Kullok et al. | 434/258 |
| 2004/0254617 A1* | 12/2004 | Hemmerling et al. | 607/48 |
| 2007/0191743 A1* | 8/2007 | McBean et al. | 601/5 |
| 2008/0234781 A1* | 9/2008 | Einav et al. | 607/48 |
| 2009/0082691 A1* | 3/2009 | Denison et al. | 600/544 |
| 2009/0259338 A1* | 10/2009 | Tong et al. | 700/258 |

* cited by examiner

*Primary Examiner* — Max Hindenburg
(74) *Attorney, Agent, or Firm* — Muncy, Geissler, Olds & Lowe, PLLC

(57) ABSTRACT

A method for quantifying an intention of movement of a user, the method comprising: extracting a mechanomyogram (MMG) signal in response to surface vibration of a muscle of the user; and averaging the MMG signal by calculating the MMG root mean squared (RMS) amplitude or frequency variance in a predetermined time window; where an increasing RMS amplitude of the MMG signal corresponds to increasing muscle voluntary contraction or a decreasing frequency variance of the MMG signal corresponds to increasing muscle voluntary contraction.

22 Claims, 14 Drawing Sheets

METHOD AND SYSTEM FOR QUANTIFYING AN INTENTION OF MOVEMENT OF A USER

TECHNICAL FIELD

The invention concerns a method and system for quantifying an intention of movement of a user.

BACKGROUND OF THE INVENTION

Muscle contractions are composed of an electrical event associated with motor unit activation through the nervous system from the brain (i.e. intention) and subsequent mechanical events due to the interaction of the contractile proteins. An in-vivo study of muscle function often involves recording the action potentials of motor units and measuring the net force produced by agonist and antagonist muscles around a joint. In some studies, the measurements also include the transverse displacement of the skin surface over the contracting muscle which has been termed the surface mechanomyogram (MMG). The skin displacement can be deduced from measuring acceleration.

SUMMARY OF THE INVENTION

In a first preferred aspect, there is provided a method for quantifying an intention of movement of a user, the method comprising:
  extracting a mechanomyogram (MMG) signal in response to surface vibration of a muscle of the user; and
  averaging the MMG signal by calculating the MMG root mean squared (RMS) amplitude or frequency variance in a predetermined time window;
  where an increasing RMS amplitude of the MMG signal corresponds to an increasing muscle voluntary contraction or a decreasing frequency variance of the MMG signal corresponds to an increasing muscle voluntary contraction.

The frequency variance of the MMG signal may be the scale or degree of frequency being spread out in a power density spectrum (PDS).

Both RMS MMG amplitude and the frequency variance of the MMG signal may be used to estimate a level of muscle contraction.

The muscle contraction level may be normalized to a percentage of maximal voluntary contraction (MVC).

The method may further comprise instructing a robotic system according to the estimated percentage of MVC.

The RMS amplitude may be normalized as a percentage of a span between a maximal and a minimum value.

The frequency variance of the MMG signal may be normalized as a percentage of a span between a maximal and a minimum value.

The predetermined time window may be 1 second with 100 ms step forward.

In a second aspect, there is provided a system for quantifying an intention of movement of a user, the system comprising:
  a measurement unit to extract a mechanomyogram (MMG) signal in response to surface vibration of a muscle of the user;
  a signal processing unit to average the MMG signal by calculating the MMG root mean squared (RMS) amplitude or frequency variance in a predetermined time window;
  where an increasing RMS amplitude of the MMG signal corresponds to an increasing muscle voluntary contraction or a decreasing frequency variance of the MMG signal corresponds to an increasing muscle voluntary contraction.

The system may further comprise another signal processing unit to pre-process a raw signal corresponding to the surface vibration of a muscle of the user.

The system may further comprise a modeling unit to translate the RMS amplitude signal and the frequency variance of the MMG signal into a set of instructions for recording or actuating a robot or an actuation unit of the robot.

The measurement unit may comprise at least one sensor to detect surface vibration of the muscle and generate an output signal.

The measurement unit may weigh less than or is equal to five grams.

The sensor may be any one from the group consisting of: condenser microphones, piezoelectric transducers, dual-axis accelerometers, MEMS-based accelerometers and angle-measurement devices.

The output signal may be passed through a band pass filter from 2 to 40 Hz to extract the MMG signal from the output signal.

The instructions may be transmitted to a robotic system to control the robotic system.

Motion and environmental parameters of the robotic system may be recorded by sensors and transmitted back to the modeling unit via a feedback signal.

The motion parameters may include dynamic parameters such as force and torque, and kinematic parameters such as linear and angular displacement, velocities, and accelerations.

Presently, electromyography (EMG) is used for estimating the intention of the user. EMG measures the electrical properties of the muscle using an EMG signal detected by three electrodes. The three electrodes are two differential signals and one reference signal. The three electrodes are attached to one muscle. Since the EMG signal is an electrical signal of muscle, skin resistance will influence the results of measurement. Also, skin preparation such as removing dead skin and shaving skin is required for every electrode attachment. In contrast, an MMG signal measures the surface vibration of muscle and therefore skin preparation is not required. Further, the MMG measurement unit is a compact and light weight unit and it can be easily attached to the muscle.

BRIEF DESCRIPTION OF THE DRAWINGS

An example of the invention will now be described with reference to the accompanying drawings, in which.

DETAILED DESCRIPTION OF THE DRAWINGS

Figure 1:
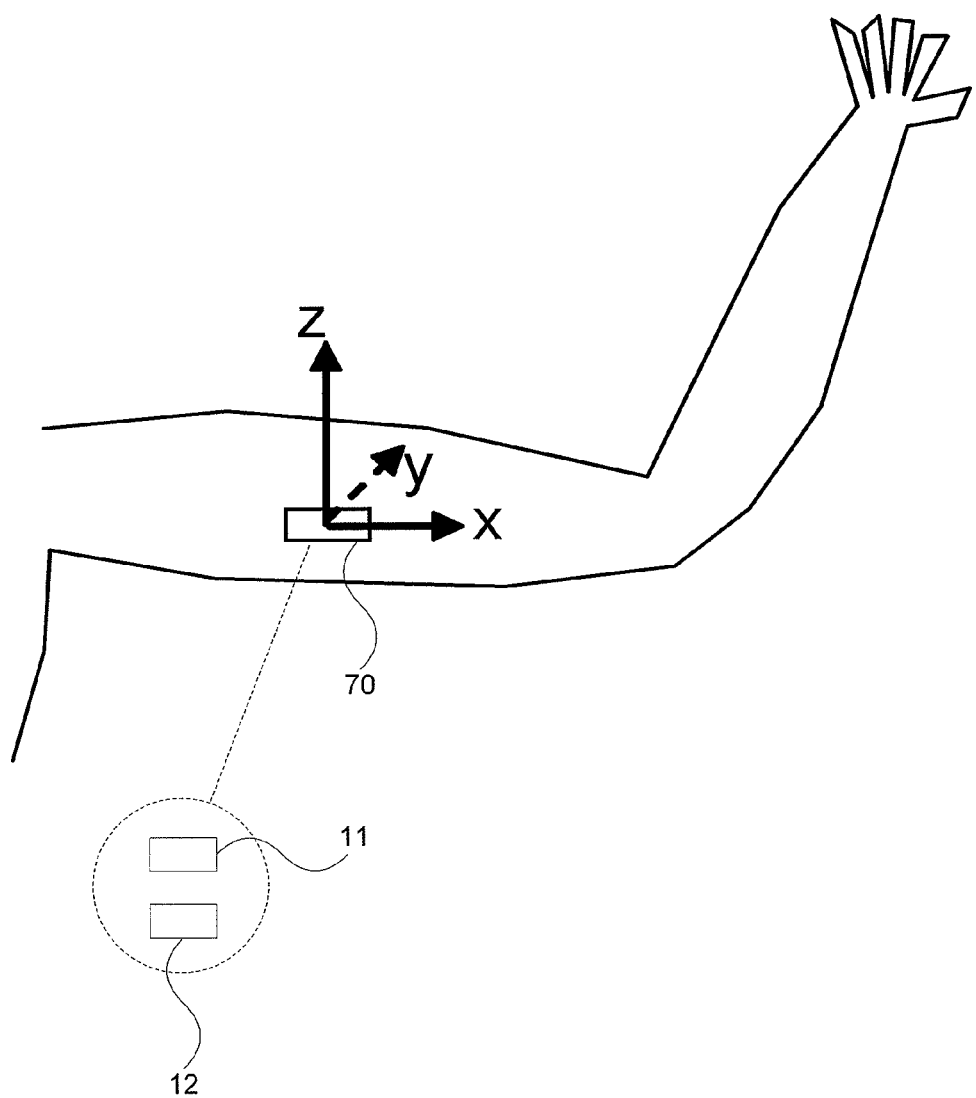
FIG. 1 is a block diagram of a muscle having two dual-axis accelerometers attached for measuring acceleration in x-y-z planes at a specific location on the muscle.

Referring to FIG. 1, two sensors 11, 12 are placed on the surface of the muscle of a user. Surface vibration of the muscle is detected by the sensors 11, 12 in order to acquire a mechanomyogram (MMG) signal. The vibration amplitude and frequency transmitted via the surface of a contacting muscle reflects the characteristics or the mechanical properties of the muscle during contraction. The MMG signal is a low frequency signal produced by lateral oscillations of contracting skeletal muscle fibers. The MMG signal relates to the number and firing rate of the recruited motor/contractile units and all of the muscle fibers are innervation. Similar to a vibrating string pivoted at both ends, the natural frequency of vibration of a muscle fiber varies inversely with the length of the muscle fiber. The MMG signal therefore corresponds to the mechanical properties of a muscle. The MMG signal is used to gauge the contraction of a muscle and also to quantify the intention of the user. In other words, certain features of the MMG signal reflect the direction of the muscle movement and amount of force of that movement intended by the user.

More than one sensor may be placed on the surface of the muscle of a user. Sensors include, for example, condenser microphones, piezoelectric transducers or MEMS-based accelerometers. The sensors 11, 12 are part of a MMG measurement unit 70. Preferably, the MMG measurement unit 70 does not weigh more than five grams otherwise the measured MMG signal may not accurately reflect the mechanical vibration on the surface of the muscle. Alternatively, only a single sensor 11 is required. The sensor 11 must be affixed on the muscle to be measured without damping or with minimal damping to ensure accuracy. In the example illustrated in FIG. 1, the sensor is an accelerometer 11 which is attached on the muscle surface. An output signal is generated by the accelerometer 11. The output signal is the acceleration generated by the contraction of the muscle. The accelerometer 11 is a dual-axis accelerometer (x-y, y-z, or x-z). This accelerometer is compact (5 mm×5 mm×2 mm leadless ceramic carrier package) and light weight (<1.0 gram).

Figure 11:
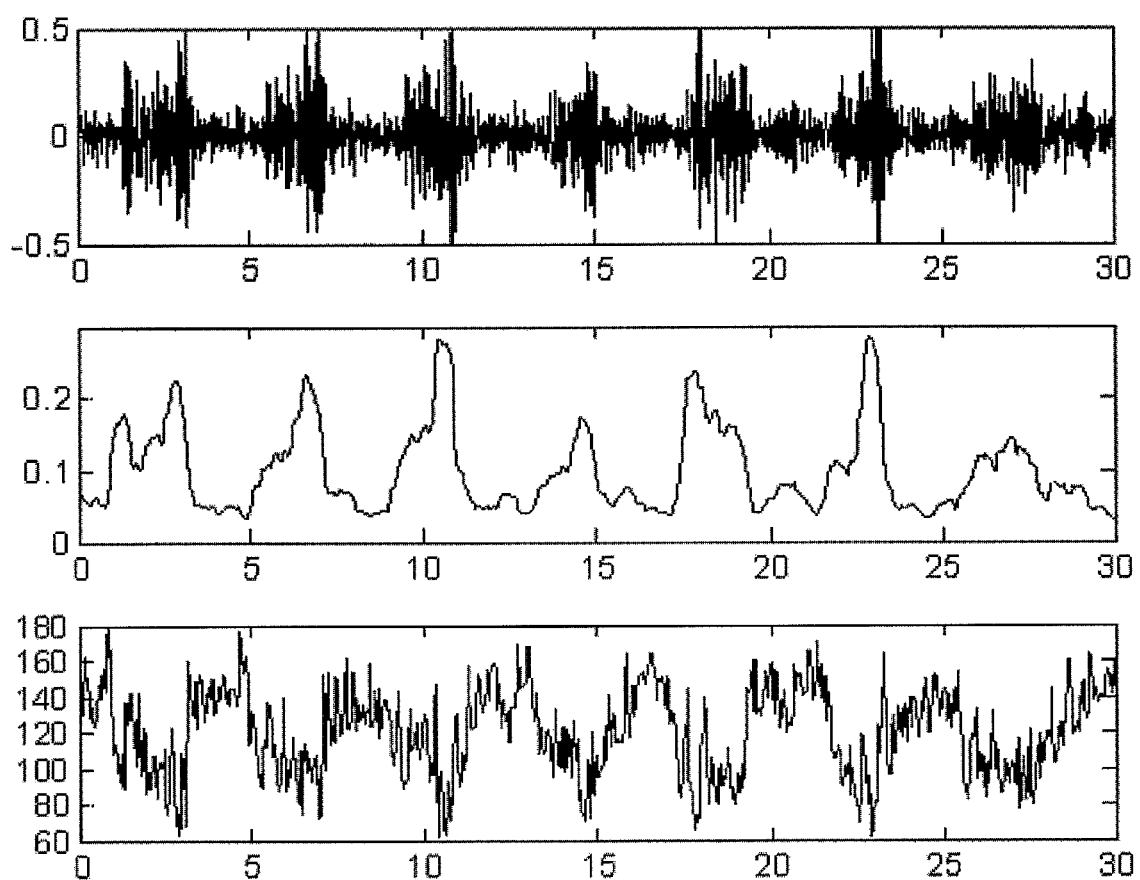
FIG. 11 is a chart illustrating the extraction of the MMG RMS amplitude and frequency variance from the filtered MMG signal.

The output signal from the accelerometer 11 consists of constant time invariant acceleration (gravity), time-varying acceleration (MMG signal) and environmental/background vibrational noise. The MMG signal is extracted from the output signal by passing through a band pass filter between 2 and 40 Hz. The MMG signal is recorded as the signal average within a time window of predetermined amount of time. Averaging the MMG signal is necessary because muscle contraction is typically not stationary or time invariant. An example time window is illustrated in FIG. 11 to extract the MMG RMS amplitude and frequency variance from the filtered MMG signal. The time window is set as 1 second with 100 ms step forward. The first time window is from 0 to 1 second, the second time window is from 0.1 to 1.1 second and so forth. The data of the filtered MMG signal in each time window is used to calculate the MMG RMS amplitude and frequency variance.

A series of signal processing techniques is applied to the MMG signal to extract the desired features of the MMG signal and model the relationship between MMG signal and muscle contraction level (torque). These desired features include root mean squared (RMS) amplitude, mean power frequency (MPF), frequency variance and frequency standard deviation. The MMG RMS amplitude and frequency variance are two important features extracted from the MMG signal. They have a close correlation to the actual muscle contraction level. These two features are also directly related to the intention of the user because the user must trigger an intention or a motive via the nervous system to the muscle. This affects muscle mechanical activity and in turn the MMG signal.

Figure 2:
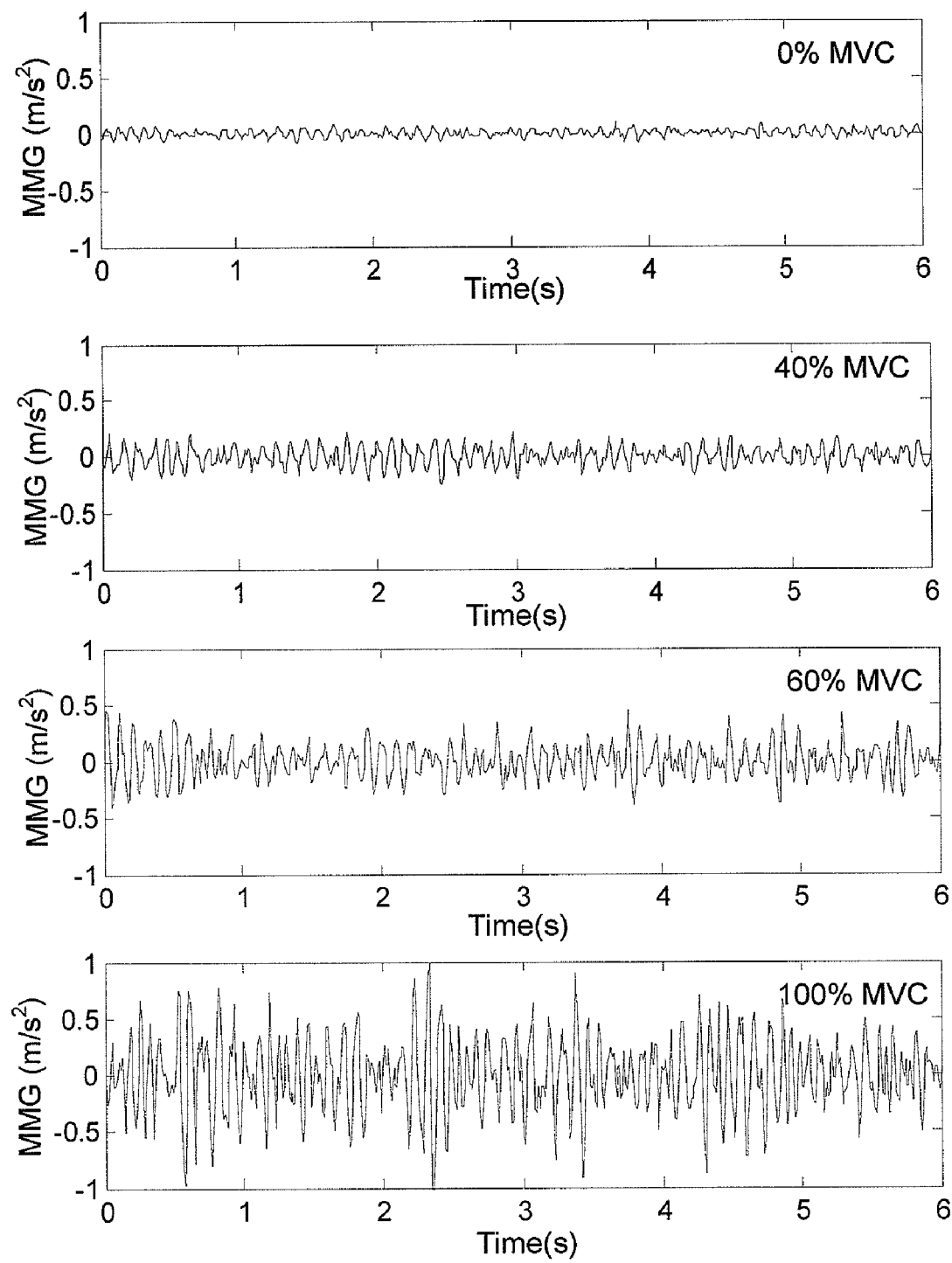
FIG. 2 is a series of charts, each chart illustrating an MMG signal during voluntary contractions of 0%, 40%, 60% and 100% maximal voluntary contraction (MVC), respectively.
Figure 3:
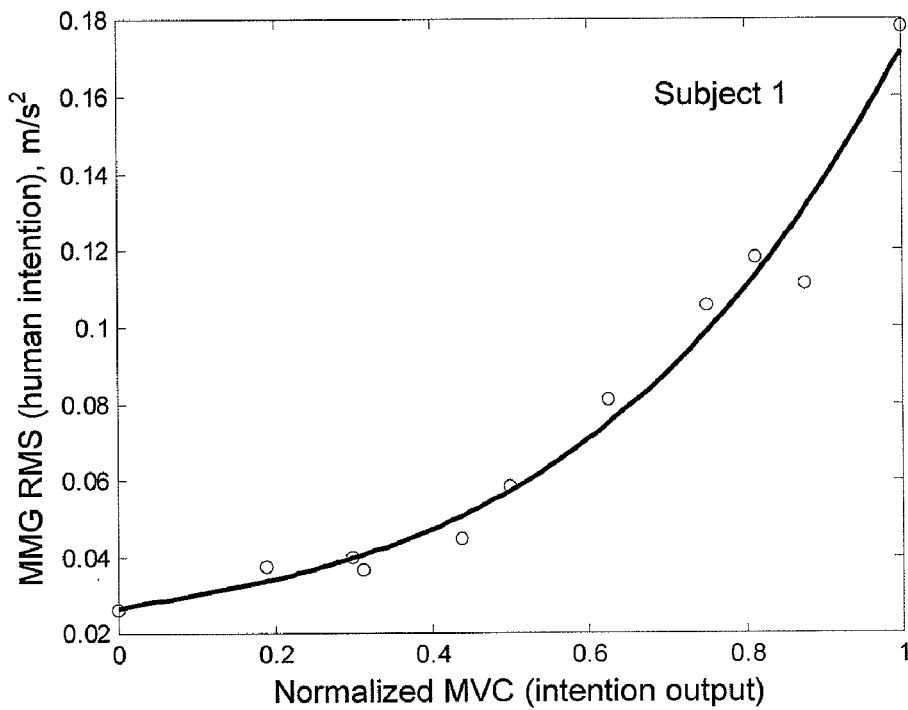
FIG. 3 is a series of charts illustrating MMG RMS to indicate the intention of the a first and second subject, and the intention is directly related to the normalized torque indicating the intention output.
Figure 3:
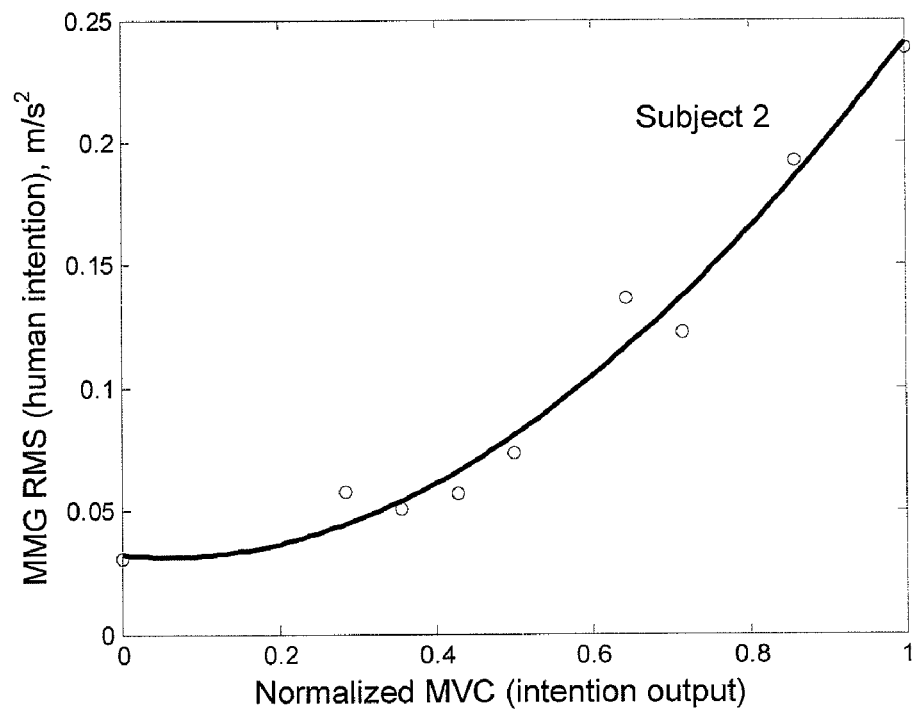

Muscle tension is monotonically related to the root mean squared (RMS) amplitude and frequency variance of the MMG signal. An MMG signal under different muscle contraction levels is shown in FIG. 2. The measured MMG amplitude increases when the muscle contraction level increases as shown in FIG. 3 for two test subjects. The muscle contraction level is normalized in FIG. 3. The normalized muscle contraction level is represented by a percentage of maximal voluntary contraction (MVC). Generally, an increasing RMS amplitude of the MMG signal is due to an increasing muscle contraction as depicted in FIG. 3. The RMS amplitude can be normalized as a percentage of a span between a maximal and a minimum value, and the frequency variance of the MMG signal can be normalized as a percentage of a span between a maximal and a minimum value.

Figure 4:
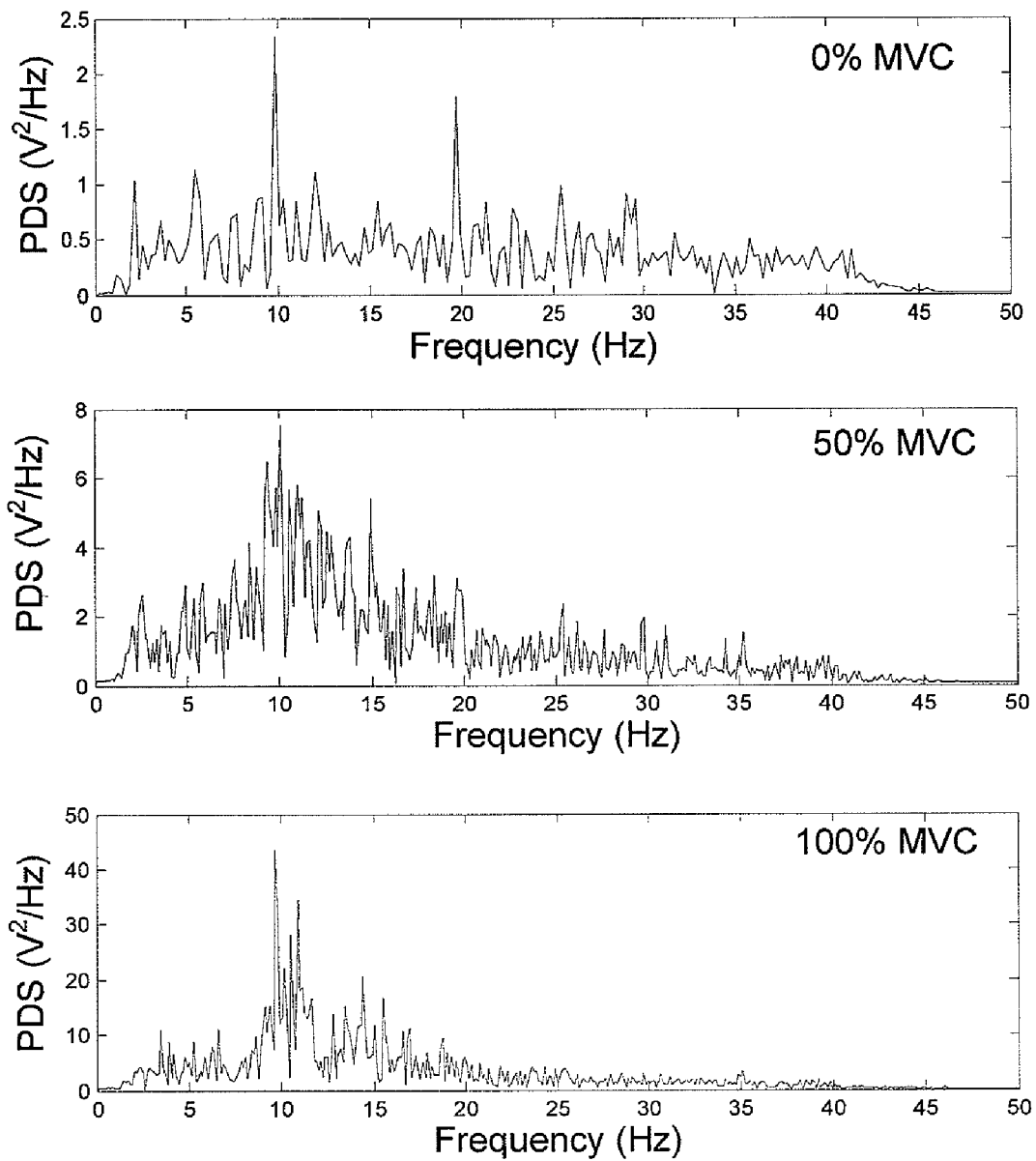
FIG. 4 is a series of power density spectrum (PDS) diagrams of an MMG signal during voluntary contractions of 0%, 50% and 100% MVC, respectively.
Figure 5:
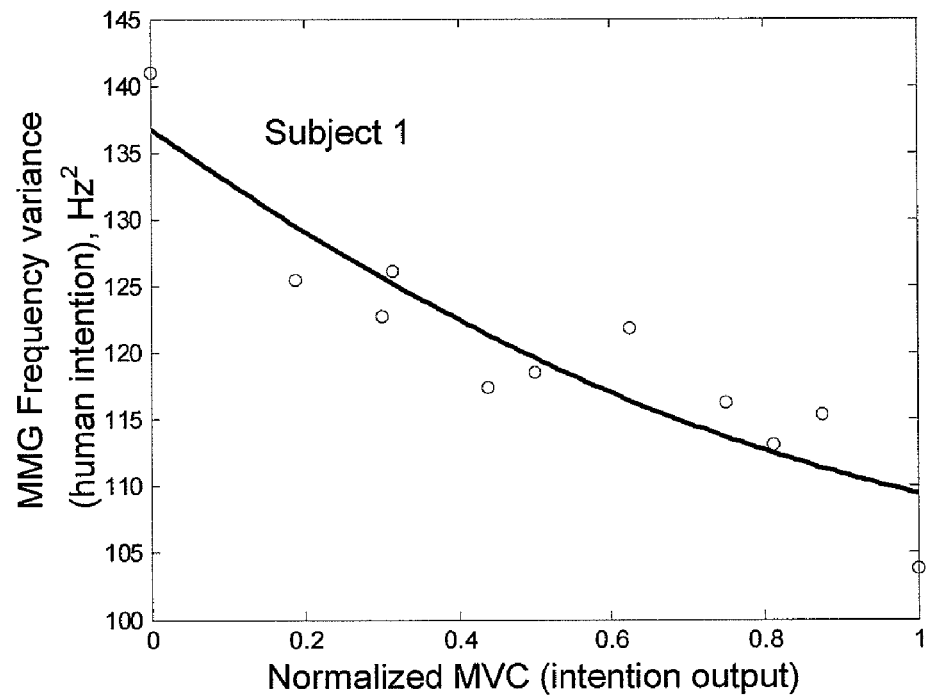
FIG. 5 is a series of charts illustrating frequency variance as a function of MVC for a first and second subject.
Figure 5:
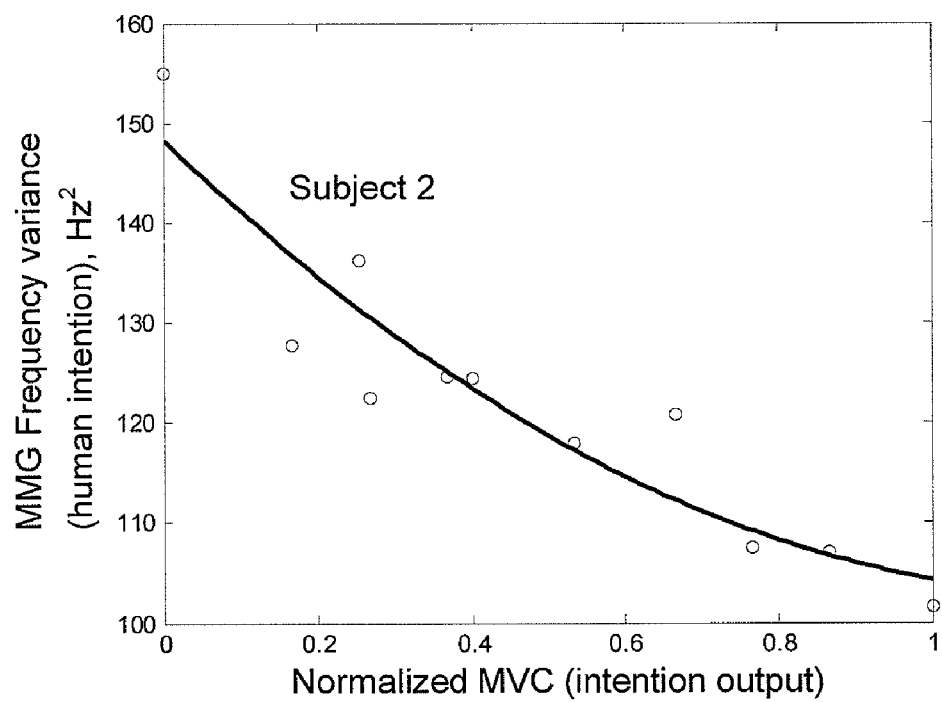
Figure 6A:
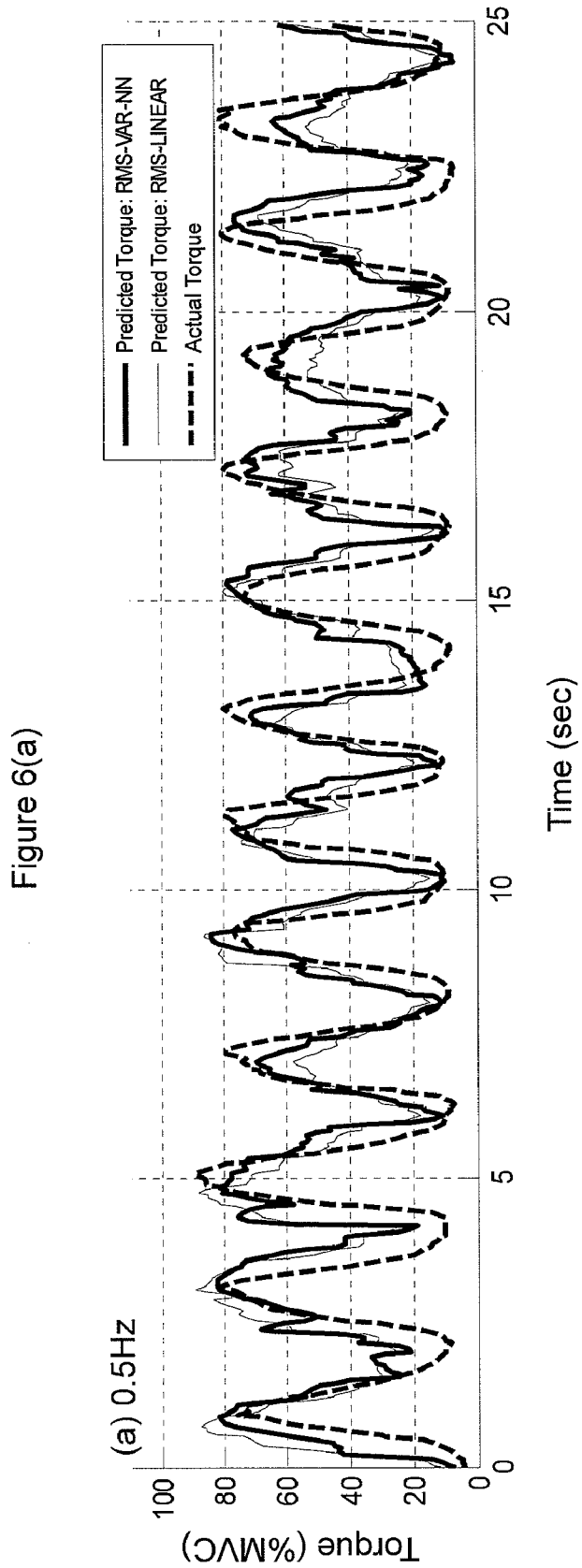
FIG. 6 is a series of four charts, each depicting an example of MMG-torque estimation for a contraction at 0.5 Hz, 0.25 Hz, 0.125 Hz and randomly.
Figure 6B:
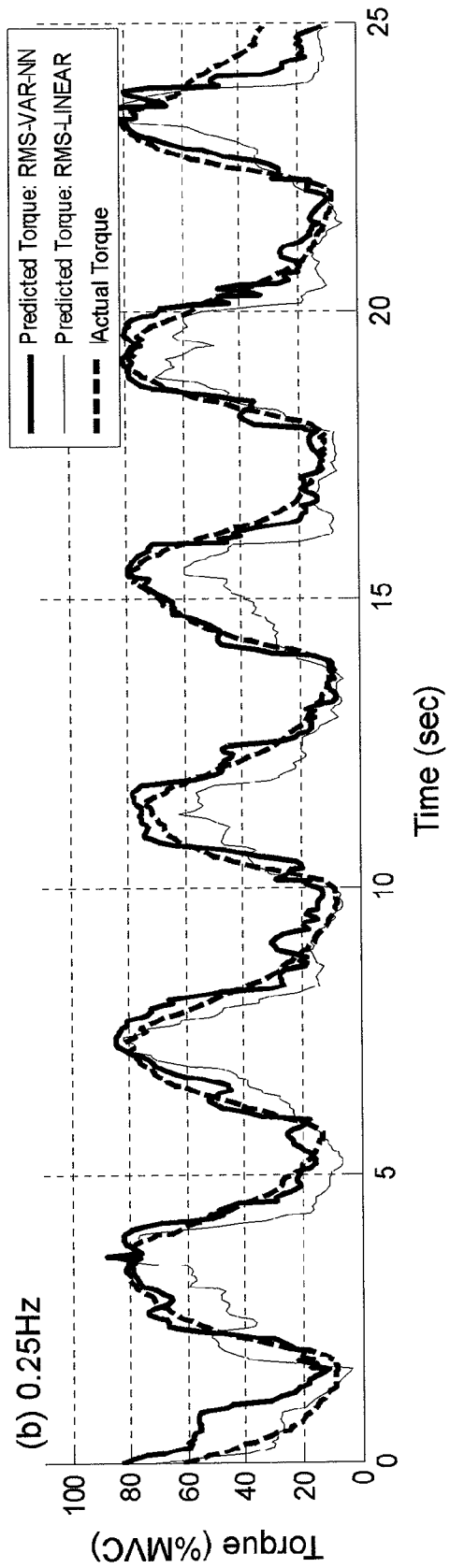
Figure 6C:
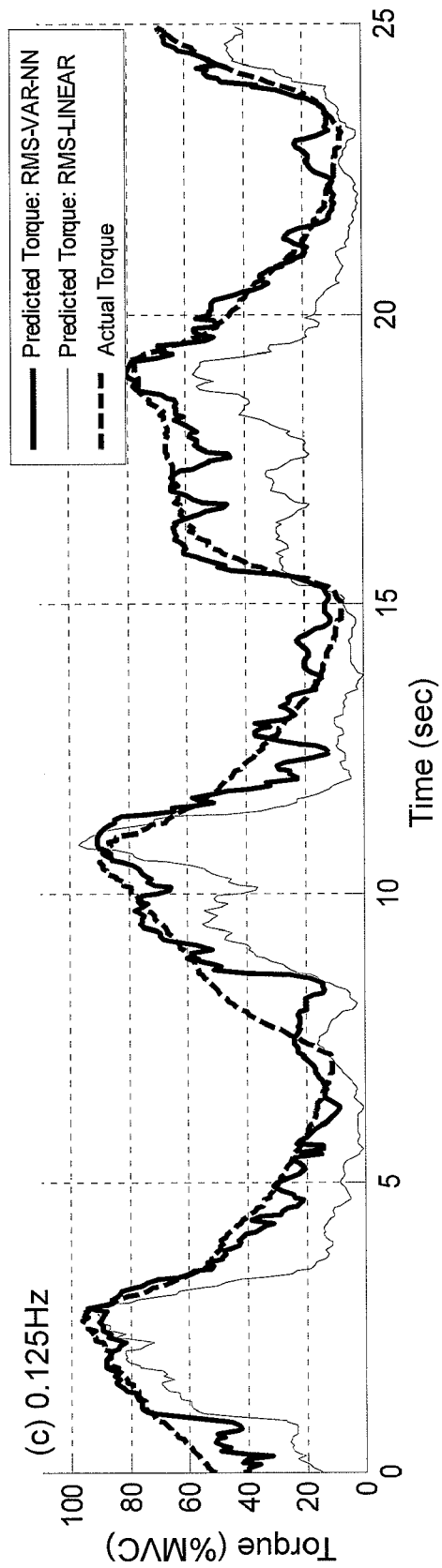
Figure 6D:
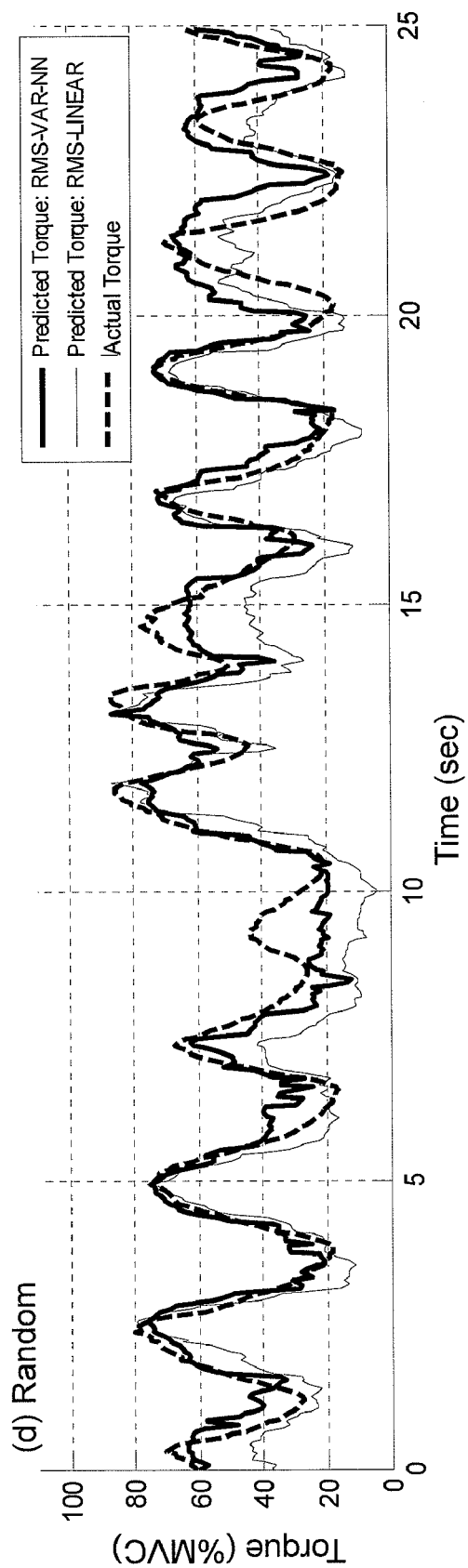

Referring to FIG. 4, a power density spectrum (PDS) diagram of the MMG signal under different muscle contraction levels is depicted. The frequency bandwidth in the PDS becomes narrower when the muscle contraction level increases. It can be represented by frequency variance which is the scale or degree of frequency being spread out. The frequency variance is the quadratic power of the standard deviation of frequency. The frequency variance decreases with an increasing muscle contraction level. This is illustrated in FIG. 5 for two test subjects.

Using both MMG RMS amplitude and frequency variance improves the accuracy of the estimate of the actual torque. However in one embodiment, either MMG RMS amplitude or frequency variance will suffice as a reasonable estimation of actual torque. FIG. 6 depicts examples of MMG torque estimation. Subjects in the examples were instructed to perform contraction at (a) 0.5 Hz, (b) 0.25 Hz, (c) 0.125 Hz, and (d) randomly. The predicted torque from MMG-torque estimator with MMG RMS and frequency variance as inputs are plotted in a thick solid line. The predicted torque from MMG RMS linear mapping are plotted in a light solid line. The actual torque from a dynamometer is plotted in a dashed line as a reference of comparison purposes.

The mean absolute error of MMG-torque estimator (RMS-VAR-NN) and linear mapping (RMS-LINEAR) at different contraction frequencies are provided in the table below:

| | Contraction frequency | | | |
|---|---|---|---|---|
| Estimator | 0.5 Hz | 0.25 Hz | 0.125 Hz | Random |
| RMS-VAR-NN | 11.26 | 6.22 | 7.01 | 7.31 |
| RMS-LINEAR | 12.03 | 10.90 | 14.81 | 10.38 |

RMS-VAR-NN corresponds to using both MMG RMS amplitude and frequency variance as inputs. RMS-LINEAR uses only MMG RMS amplitude as an input. It is apparent that RMS-VAR-NN is more accurate than RMS-LINEAR because it consistently conforms closer to the actual torque measured by the dynamometer.

Figure 7:
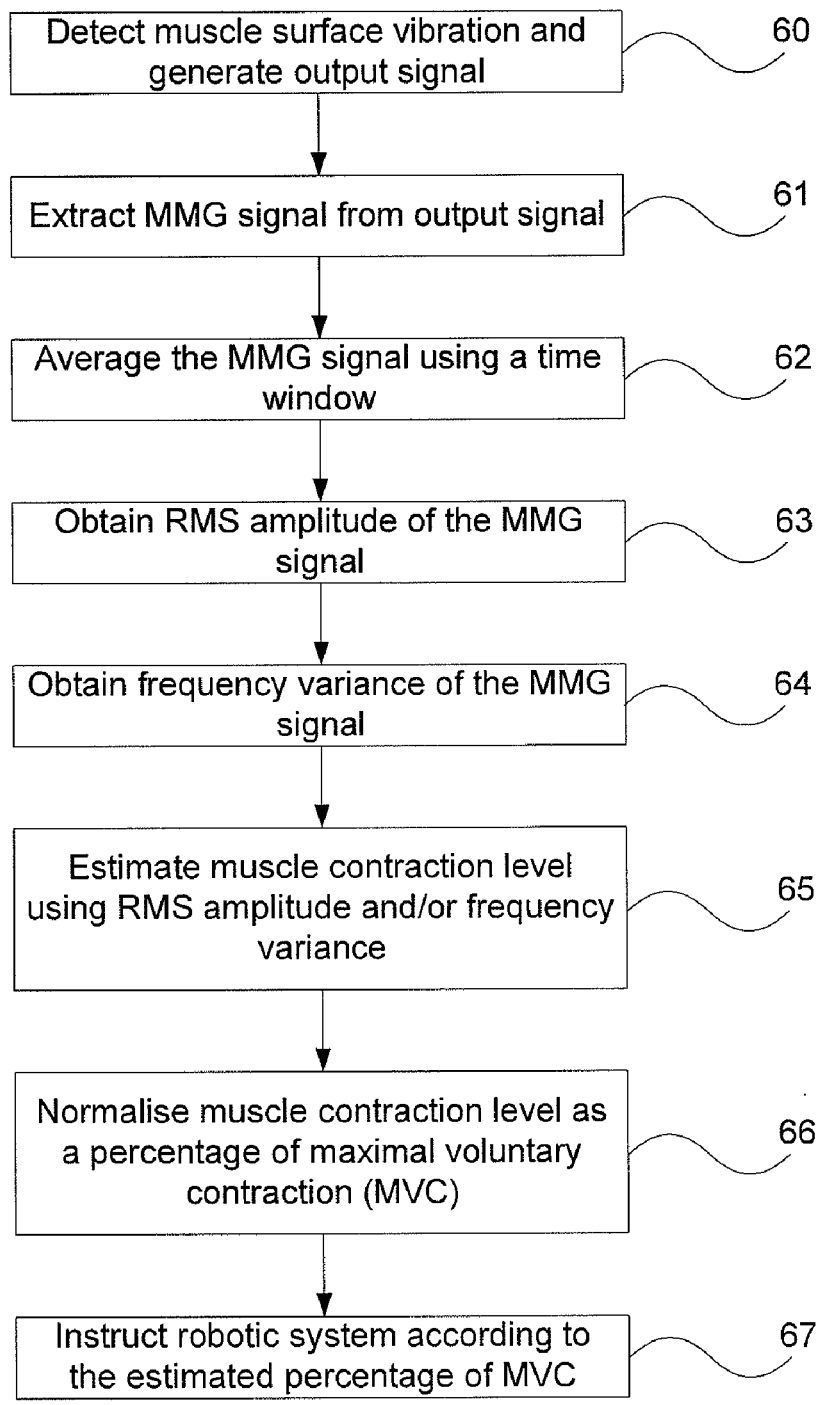
FIG. 7 is a process flow diagram of acquiring and using the MMG signal.

Referring to FIG. 7, in a typical scenario, the acquisition and use of an MMG signal is depicted. Surface vibration of the muscle is detected by a sensor and the sensor generates (60) an output signal. The MMG signal is extracted (61) from the output signal via a filter. The MMG signal is averaged (62) using a time window. The RMS amplitude of the MMG signal is obtained (63). The frequency variance of the MMG signal is obtained (64). The muscle contraction level is estimated (65) using the RMS amplitude and/or the frequency variance of the MMG signal. The muscle contraction level is normalized (66) as a percentage of MVC. The percentage of MVC is used to instruct and control (67) a robotic system.

Figure 8:
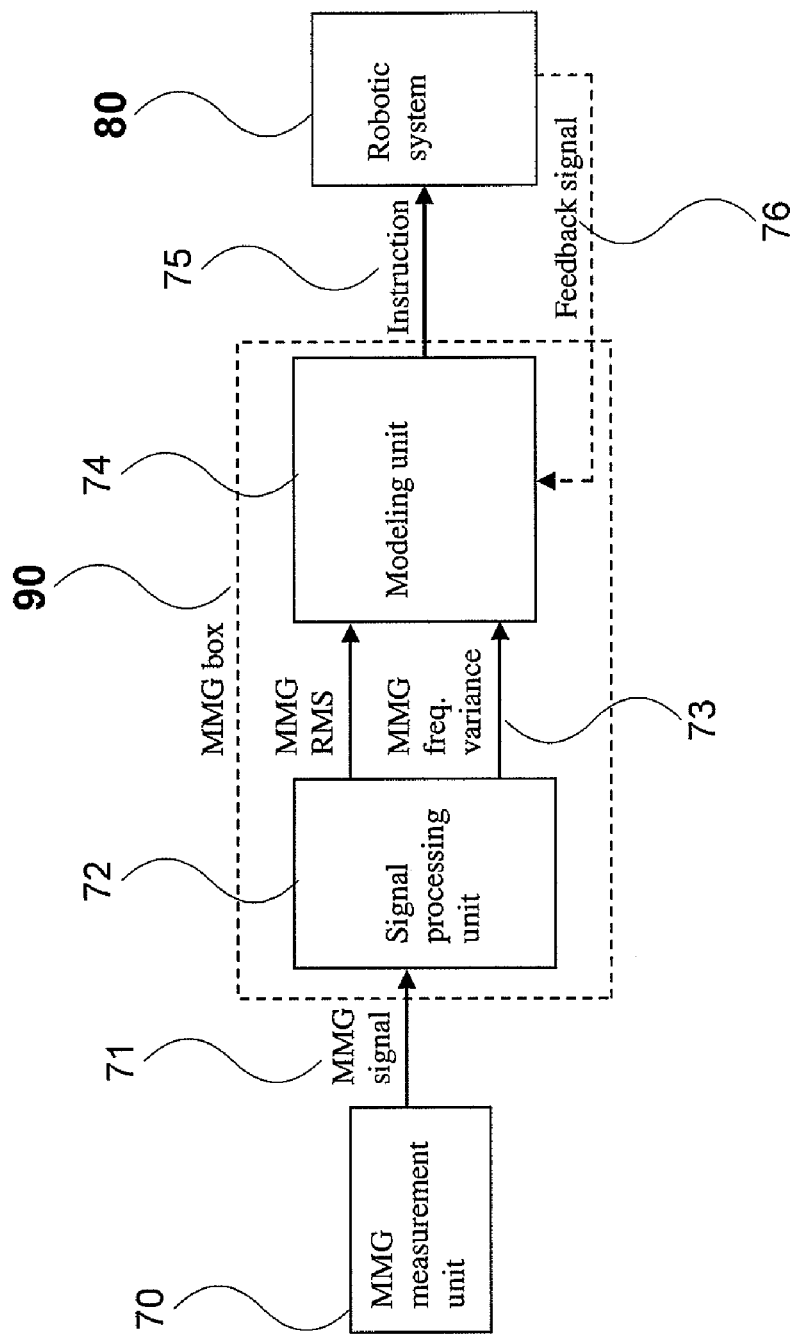
FIG. 8 is a block diagram of robot control system that is controlled using an MMG signal.

Referring to FIG. 8, intelligent algorithms such as neural networks, fuzzy logic and control algorithms are able to model the relationship between MMG signal and the muscle contraction level using the inputs of MMG RMS amplitude and frequency variance. Therefore, robotic systems 80 assisting human physical motion, such as torque, force, speed, and position can be instructed using human intention via acquiring and processing an MMG signal. When the input of a robotic system 80 is supplied by human physical motion, the MMG measurement unit 70 measures the MMG signal 71 generated by a specific contracting muscle. The signal processing unit 72 processes the raw MMG signal 71 to acquire some desired features of the MMG signal 71. Another signal processing unit to pre-process a raw signal corresponding to the surface vibration of a muscle of the user. The desired features include MMG amplitude and frequency variance 73. These features may be used individually or in combination. A modeling unit 74 translates these features into a set of instructions 75 for a robotic system 80 to understand.

A further improvement is to use the actual torque, force, speed and position of the robotic system 80 as a feedback to determine the difference in intended motion versus the actual motion. The difference is considered the error or inaccuracy. The motion parameters of the robotic system 80 are recorded by sensors. The motion parameters include torque, force, speed, and position of the robotic system 80. These are fed back to the modeling/control unit 74 via feedback signals 76. For example, to control a robot for muscle training, a user pushes a control bar to move the robot forward. The bar provides a certain level resistance. The modeling unit 74 calculates the muscle contract level/produced force of the user and determines how much resistant force is to be produced by the bar. After the calculation, the modeling unit 74 transmits the resistance value as an instruction to the bar. Accordingly, the bar provides the exact amount of resistance to the user.

As another example, one can use the normalized MMG signals (either RMS amplitude and frequency variance) as control of the normalized torque per the general calibration on all users or customized to a specific user.

Figure 9:
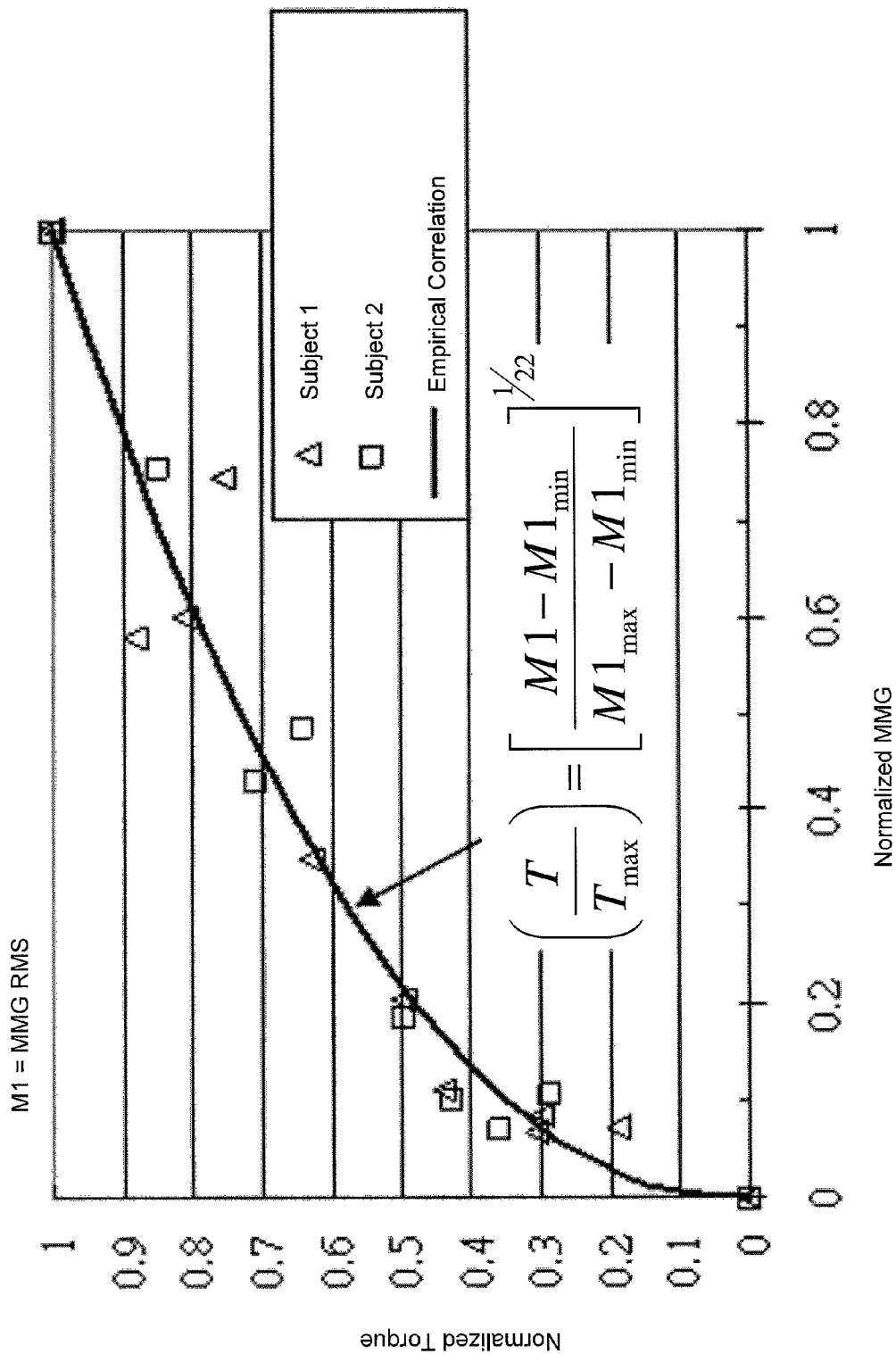
FIG. 9 is a normalized chart of torque versus normalized MMG signal in the form of RMS amplitude.
Figure 10:
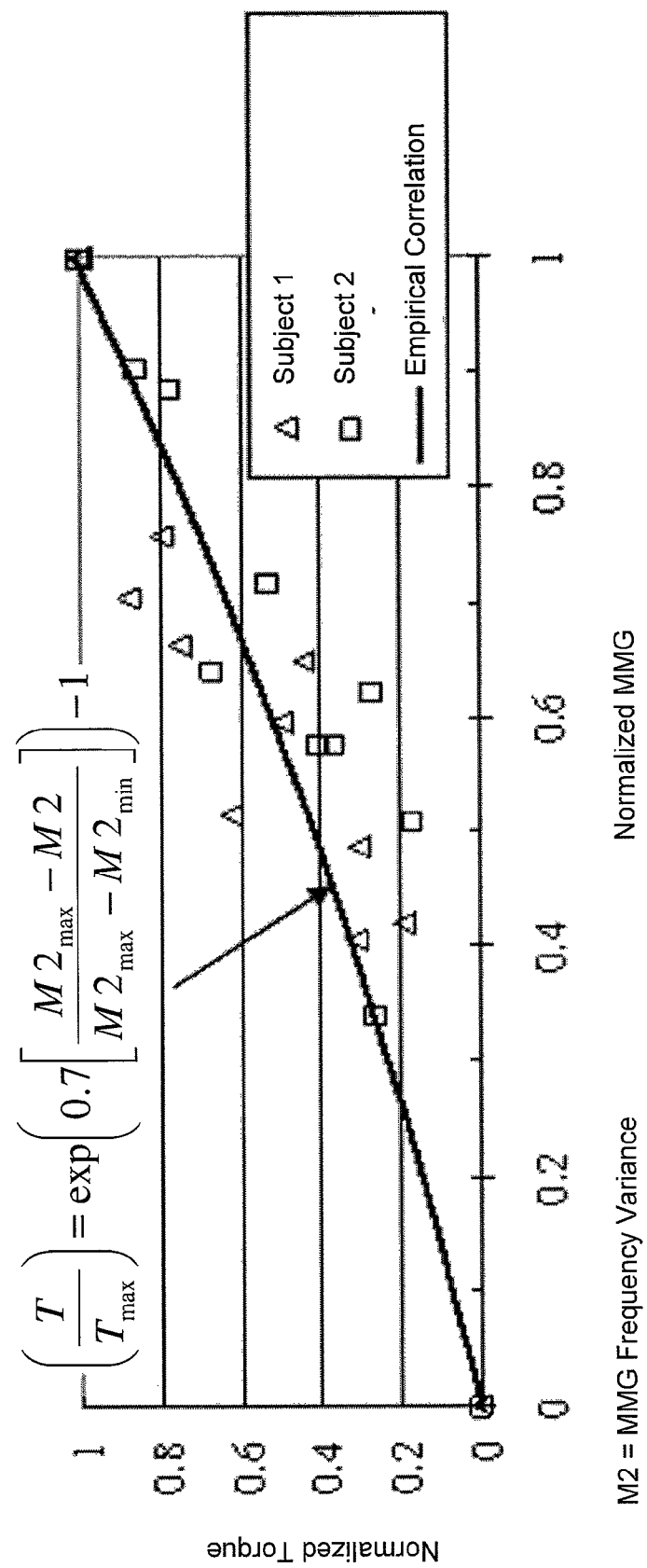
FIG. 10 is a normalized chart of torque versus normalized MMG signal in the form of frequency variance.

FIGS. 9 and 10 show the normalized MVC/torque to the normalized MMG signal in terms of the RMS amplitude and frequency variance, respectively. The following is an algorithm of the torque for rehabilitation of a stroke patient:

$$T_{total} = gT - T_r$$

where $$\left(\frac{T}{T_{max}}\right) = \left[\frac{M1 - M1_{min}}{M1_{max} - M1_{min}}\right]^{\frac{1}{22}}$$

and M1 is the RMS amplitude, or $$\left(\frac{T}{T_{max}}\right) = \exp\left(0.7\left[\frac{M2_{max} - M2}{M2_{max} - M2_{min}}\right]\right) - 1$$

and M2 is the frequency variance. $T_r$=resistive torque=constant and g=0 to 1 (gain factor)

Both signal processing and modeling units 72, 74 may be packaged as a black box referred to as the MMG box 90. The black box provides instruction to the robot 80 by receiving MMG signal from the muscles of the body, and optionally receiving additional feedback signals (actual torque/force, speed, position, etc.) of the robot 80. The input of MMG box 90 is the raw MMG signal 71 and the output is the instruction 75 for the robotic system 80. The MMG box 90 may be used for all existing robotic systems including gaming, rehabilitation and training.

The MMG box 90 may be integrated with muscle-training rehabilitation equipment for various users including stroke patients and the elderly; sports equipment for athletes; or gaming equipment for teenagers. The MMG box 90 is able to gauge the user's intention and then output a signal to the robotic device 80 to provide certain assistance/resistance torque or force.

An embedded system may integrate all algorithms into a single micro-processor. A compact MMG box is envisaged and implemented for various applications.

It will be appreciated by persons skilled in the art that numerous variations and/or modifications may be made to the invention as shown in the specific embodiments without departing from the scope or spirit of the invention as broadly described. The present embodiments are, therefore, to be considered in all respects illustrative and not restrictive.

We claim:

1. A method for determining an intention of movement of a user, the method comprising:
    extracting a mechanomyogram (MMG) signal from one or more vibration sensors in response to surface vibration of a muscle of the user;
    averaging the MMG signal by calculating the MMG root mean squared (RMS) amplitude or frequency variance in a predetermined time window;
    determining a change in the RMS amplitude or frequency variance of the MMG signal over time, wherein an increasing RMS amplitude or a decreasing frequency variance of the MMG signal is used to identify a voluntary contraction of the muscle; and
    determining an intention of the user to contract the muscle based on the determined change in the RMS amplitude or frequency variance of the MMG signal.

2. The method according to claim 1, wherein the frequency variance of the MMG signal is the scale or degree of frequency being spread out in a power density spectrum (PDS).

3. The method according to claim 1, wherein both RMS MMG amplitude and the frequency variance of the MMG signal are used to estimate a level of muscle contraction.

4. The method according to claim 1, wherein the muscle contraction level is normalized to a percentage of maximal voluntary contraction (MVC).

5. The method according to claim 4, further comprising instructing a robotic system according to the estimated percentage of MVC.

6. The method according to claim 1, wherein the RMS amplitude is normalized as a percentage of a span between a maximal and a minimum value.

7. The method according to claim 1, wherein the frequency variance of the MMG signal is normalized as a percentage of a span between a maximal and a minimum value.

8. The method according to claim 1, wherein the predetermined time window is 1 second with 100 ms step forward.

9. A system for determining an intention of movement of a user, the system comprising:
- a measurement unit to extract a mechanomyogram (MMG) signal using one or more vibration sensors in response to surface vibration of a muscle of the user; and
- a signal processing unit to average the MMG signal by calculating the MMG root mean squared (RMS) amplitude or frequency variance in a predetermined time window, to determine a change in the RMS amplitude or frequency variance of the MMG signal over time, wherein an increasing RMS amplitude or a decreasing frequency variance of the MMG signal is used to identify a voluntary contraction of the muscle, and to determine an intention of the user to contract the muscle based on the determined change in the RMS amplitude or frequency variance of the MMG signal.

10. The system according to claim 9, further comprising another signal processing unit to pre-process a raw signal corresponding to the surface vibration of a muscle of the user.

11. The system according to claim 9, further comprising a modeling unit to translate the RMS amplitude signal and the frequency variance of the MMG signal into a set of instructions for recording or actuating a robot or an actuation unit of the robot.

12. The system according to claim 9, wherein the measurement unit comprises at least one sensor to detect surface vibration of the muscle and generate an output signal.

13. The system according to claim 9, wherein the measurement unit weighs less than or is equal to five grams.

14. The system according to claim 12, wherein the sensor is any one from the group consisting of: condenser microphones, piezoelectric transducers, dual-axis accelerometers, MEMS-based accelerometers and angle-measurement devices.

15. The system according to claim 12, wherein the output signal is passed through a band pass filter from 2 to 40 Hz to extract the MMG signal from the output signal.

16. The system according to claim 9, wherein the instructions are transmitted to a robotic system to control the robotic system.

17. The system according to claim 11, wherein motion and environmental parameters of the robotic system are recorded by sensors and transmitted back to the modeling unit via a feedback signal.

18. The system according to claim 17, wherein the motion parameters include dynamic parameters of: force or torque, and kinematic parameters any one from the group consisting of: linear and angular displacement, velocities, and accelerations.

19. The method according to claim 1, wherein the vibration sensors include condenser microphones, piezoelectric transducers, and/or MEMS-based accelerometers.

20. The method according to claim 1, wherein the quantifying comprises determining a direction of movement of the muscle and/or an amount of force intended by the user for moving the muscle.

21. The method according to claim 1, wherein the frequency variance comprises a scale or a degree of the frequency being spread out.

22. The system according to claim 9, wherein the frequency variance comprises a scale or a degree of the frequency being spread out.

* * * * *